United States Patent [19]

DeVries et al.

[11] Patent Number: 4,527,557
[45] Date of Patent: Jul. 9, 1985

[54] MEDICAL VENTILATOR SYSTEM

[75] Inventors: Douglas F. DeVries, Redlands; Arie Cohen, Walnut, both of Calif.

[73] Assignee: Bear Medical Systems, Inc., Riverside, Calif.

[21] Appl. No.: 667,115

[22] Filed: Nov. 1, 1984

[51] Int. Cl.³ ............................................. A61M 16/00
[52] U.S. Cl. ........................... 128/204.23; 128/204.25; 128/205.24
[58] Field of Search ....................... 128/204.21, 204.22, 128/204.23, 204.25, 204.26, 205.24; 251/133, 251

[56] References Cited

U.S. PATENT DOCUMENTS

| | | | |
|---|---|---|---|
| 3,028,860 | 4/1962 | Gagnan et al. | 128/204.26 |
| 3,903,881 | 9/1975 | Weigl | 128/145.6 |
| 4,036,221 | 7/1977 | Hillsman et al. | 128/145.6 |
| 4,097,786 | 6/1978 | Lund | 318/282 |
| 4,204,536 | 5/1980 | Albarda | 128/204.22 |
| 4,262,689 | 4/1981 | Rodder | 137/246.12 |
| 4,323,064 | 4/1982 | Hoenig | 128/204.21 |
| 4,326,513 | 4/1982 | Schulz et al. | 128/203.14 |
| 4,333,453 | 5/1982 | Rodder | 128/205.24 |
| 4,336,590 | 6/1982 | Jacq et al. | 364/418 |
| 4,344,144 | 8/1982 | Damico et al. | 128/204.22 X |
| 4,345,612 | 8/1982 | Koni et al. | 137/101.19 |
| 4,401,116 | 8/1983 | Fry et al. | 128/205.24 |
| 4,448,192 | 5/1984 | Stawitcke et al. | 128/204.26 |

Primary Examiner—D. E. Gantz
Assistant Examiner—Glenn A. Caldarola
Attorney, Agent, or Firm—Howard J. Klein; Gabor L. Szekeres

[57] ABSTRACT

A volume ventilator is disclosed which has a balloon valve type exhalation valve for permitting release of gases to the ambient environment during the exhalation period of artificial ventilation or spontaneous breathing, or when there is excess proximal pressure in the ventilator system. A pressure transducer continuously senses the proximal pressure in the ventilator system and sends to a microcomputer controller and associated circuitry of the ventilator system a signal indicative of the instantaneous proximal pressure. The pressure in the balloon, which is the pilot pressure of the exhalation valve, is regulated through a jet venturi type pressure controller which is connected to a source of pressurized gas. The gas flows through the jet venturi, wherein its flow rate is regulated by a ball valve moving against a suitable valve seat. The ball valve is controlled by a stepper motor through a cam follower. The stepper motor is controlled through electronic signals generated in the computer control in response to the difference between the instantaneously sensed proximal pressure, and the pilot pressure required to be present in the balloon in accordance with an algorithm or preselected pilot pressure-versus-time function. Accurate servo control of the flow of respiratory gas to the patient is accomplished by a flow control subsystem which incorporates a flow control valve controlled by a second stepper motor. The flow of the respiratory gas is monitored, downstream of the flow control valve, by a flow transducer. The flow transducer sends to the microcomputer controller a signal indicative of the instantaneous flow rate of the respiratory gas. The microcomputer controller compares the instantaneous flow rate to a flow rate value required by an algorithm or preselected flow rate-versus-time function stored in its memory. The microcomputer controller then sends a signal to the second stepper motor to adjust the flow control valve to provide the flow rate instantaneously required by the preselected function or algorithm.

34 Claims, 4 Drawing Figures

FIG.1

MEDICAL VENTILATOR SYSTEM

BACKGROUND OF THE INVENTION

1. Field of the Invention

The present invention is directed to ventilator systems which provide respiratory gas for artificial respiration of a patient. More particularly, the present invention is directed to volume ventilator systems which have improved control over the flow rate and pressure parameters of the respiratory gas which is made available to the patient.

2. Brief Description of the Prior Art

Artificial ventilators, or ventilator systems which provide air, or air and oxygen mixtures for artificial respiration by a patient, are well known in the art.

One type of artificial ventilator of the prior art is generally known as a "pressure ventilator", because, in operation, such ventilators make the respiratory gas available to the patient in accordance with a substantially predetermined pressure-versus-time cycle.

Another type of artificial ventilator of the prior art is known as a "volume ventilator", because such ventilators make a predetermined volume of respiratory gas available to the patient in each breathing cycle. In other words, "volume ventilators" deliver the respiratory gas to the patient in accordance with a predetermined volume-versus-time, or flow rate-versus-time function.

As is well understood by those skilled in the art, an artificial ventilator should, ideally, be capable of accurately monitoring several parameters of the artificial ventilation process, and of reliably maintaining those parameters within predetermined limits. More specifically, the parameters which should be accurately and reliably maintained include the percentage of oxygen in the respiratory gas (when a mixture of air and oxygen, rather than just air, is prescribed for the patient), the flow rate of the respiratory gas to the patient, and the pressure of the gas in the system which is proximal to the patient (proximal pressure).

As noted above, a volume ventilator operates on the basic principle that a predetermined volume of respiratory gas is delivered to the patient in each breathing cycle. The flow rate of the gas, however, is not necessarily constant during the cycle. Rather, the respiratory gas is often delivered to the patient in accordance with a predetermined flow-rate-versus-time (or, what is essentially an equivalent, predetermined volume-versus-time) curve, determined by a physician in a prescription tailored to the individual requirements of the patient.

The proximal pressure of the respiratory gas (like the flow rate) is usually also not kept constant in prior art ventilators. Rather, during certain modes of ventilation the proximal pressure is usually controlled by an exhalation valve which opens and closes to maintain a predetermined pressure level in the system. However, the pressure level maintained by the exhalation valve is not constant during the ventilation cycle. Rather, it varies in a time cycle to permit inflation of the patient's lungs with respiratory gas, and thereafter to permit deflation down to a predetermined pressure level, while the patient exhales. Furthermore, the exhalation valve also functions as an important safety valve, to minimize the possibility of accidental "overpressurization" of the patient.

In addition to the foregoing briefly summarized requirements, artificial ventilators must, or at least ideally should, operate very reliably and safely. Safety, for example, requires not only accurate maintenance of the control parameters of the ventilation process, but also rapid access to ambient air to allow the natural breathing of the patient when an electrical power failure or other serious malfunction occurs in the system.

Still further, artificial volume ventilators ideally should be able to deliver several types of breaths, such as "volume controlled" breath where the ventilator entirely provides the breathing effort of the patient (briefly described above), and "assisted volume controlled" breath and "spontaneous" breath. In the latter two types of breath the ventilator detects and assists or supports the spontaneous breathing efforts of the patient.

The prior art has developed several ventilators in efforts to more-or-less satisfy the above-noted and other requirements. Typically, prior art volume ventilators include a blender for providing a mixture of air and oxygen of a predetermined concentration, a computer assisted flow control subsystem, and a computer assisted pressure control subsystem. The flow control subsystems of the prior art usually comprise a positive displacement piston, the movement of which is directed by a computer in accordance with a predetermined volume-(or flow) versus-time function. The pressure control subsystems of the prior art volume ventilators typically comprise a pressure regulator which outputs a pilot pressure to pneumatically control the release pressure of the exhalation valve.

Examples of prior art artifical ventilators and of specific components of such ventilators, or related systems can be found in U.S. Pat. Nos. 4,036,221; 4,177,830; 4,336,590; 4,326,513; 4,204,536; 3,903,881; 4,190,045; 4,448,192; 4,323,064; 4,262,689; 4,333,453; 4,097,786.

Although prior art ventilators have proven suitable for many clinical needs, the need has been recognized for increasingly accurately monitoring and maintaining the time cycled flow rate and proximal pressure parameters of the ventilators. Therefore, the present invention, which provides a ventilator of improved ability to accurately and reliably maintain the foregoing important parameters, represents a major step forward in the art.

SUMMARY OF THE INVENTION

It is an object of the present invention to provide an artificial ventilator which has an improved, servo controlled pressure regulator system to maintain the proximal pressure within limits set by a preselected pressure-versus-time function.

It is another object of the present invention to provide an artificial ventilator which has an improved, servo controlled flow regulator system to maintain the flow rate of respiratory gases to the patient within limits set by a preselected flow-rate versus-time function.

The foregoing and other objects and advantages are attained by a ventilator system which includes a pressure regulated source of respiratory gas, a flow control subsystem which provides a rate of flow of the respiratory gas in accordance with a preselected flow-rate-versus-time function, a pressure control subsystem including an exhalation valve in fluid communication with the proximal gases of the patient and a pilot pressure control valve which controls the exhalation valve through a pilot pressure generated in the pilot pressure control valve.

The pilot pressure control valve includes a venturi jet connected to a source of gas of substantially constant pressure and having an outlet to the ambient. The stream of gas flowing through the venturi jet to the ambient is controlled through a valve connected to a stepper motor, which is, in turn, regulated by signals from a computer. A static port in the venturi jet provides the pilot pressure for the exhalation valve.

A pressure transducer is operatively mounted in the system to sense the proximal pressure of the patient and to send a signal indicative of the instantaneous proximal pressure to the computer. The computer stores a preselected pressure-versus-time-function in its memory and compares the pressure value required by the pressure-versus-time function to the instantaneous pressure sensed by the pressure transducer. As a result of the comparison, the computer generates and sends a corrective electric signal to the stepper motor to adjust the valve so as to adjust, preferably in the next breathing cycle, the pilot pressure substantially to the value required by the stored, preselected pressure-versus-time function.

In the preferred embodiment of the ventilator system of the present invention, the flow control subsystem includes a linearly moving flow control valve actuated by an asymmetrical cam mounted to the shaft of a second stepper motor. The second stepper motor is controlled by another corrective signal sent by the computer as a result of comparing the instantaneous flow rate, as sensed by a flow transducer, to the flow rate value required by the flow rate-versus-time function stored in the computer's memory.

The present invention can be best understood, together with further objects and advantages, from the following description taken together with the appended drawings, wherein like numerals designate like parts.

DESCRIPTION OF THE PREFERRED EMBODIMENT

The following specification taken in conjunction with the drawings sets forth the preferred embodiment of the present invention. The embodiments of the invention disclosed herein are the best modes contemplated by the inventors for carrying out their invention in a commercial environment, although it should be understood that various modifications can be accomplished within the scope of the present invention.

Figure 1:
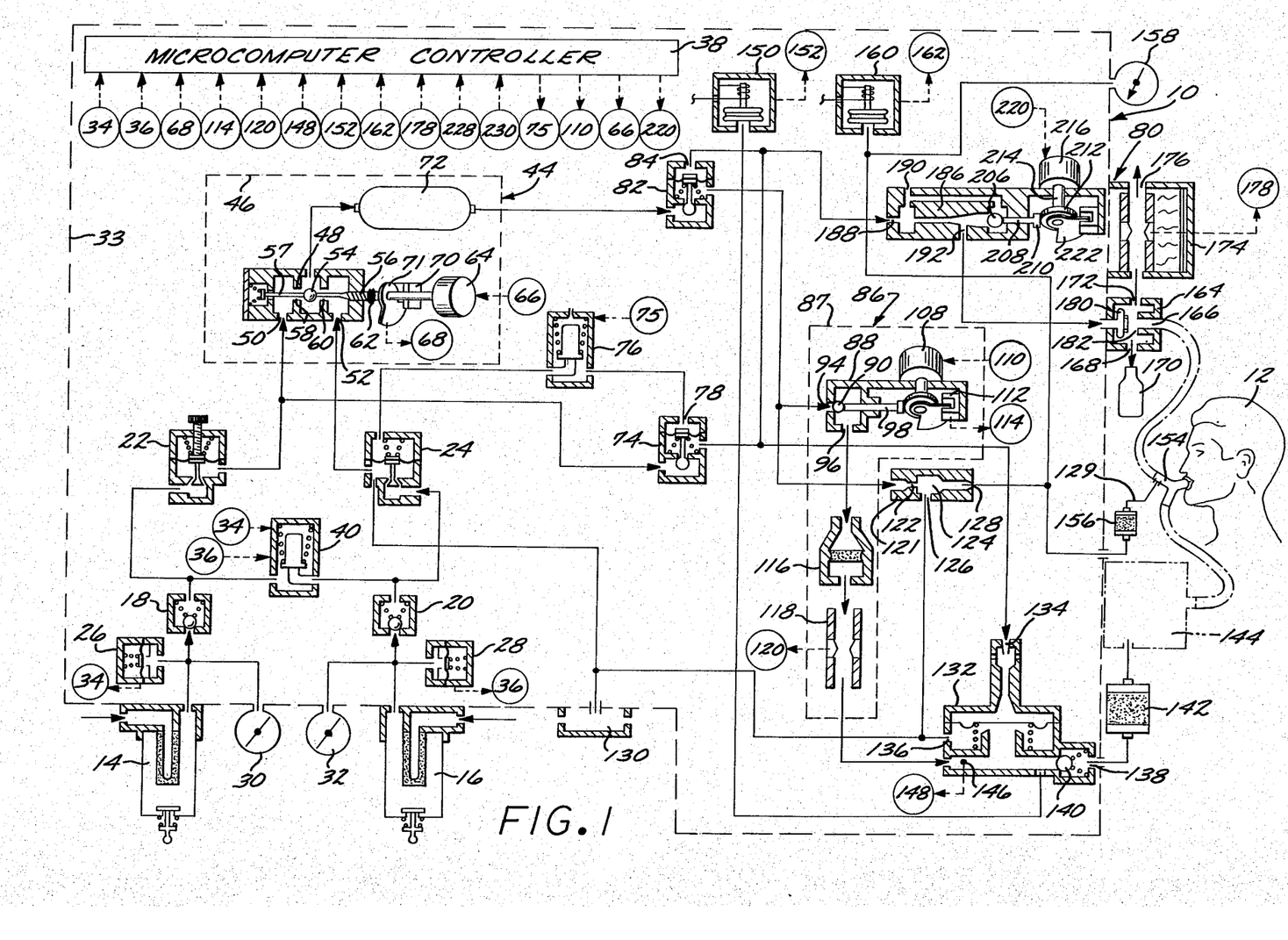
FIG. 1 is a schematic representation of the preferred embodiment of the ventilator system of the present invention.

Referring now to the schematic view of FIG. 1, a preferred embodiment of the artificial ventilator system 10 of the present invention is disclosed. The preferred embodiment of the ventilator system or ventilator 10 of the present invention is best described by following the flow path of air, or air oxygen mixtures, through the several components of the ventilator system 10 to a patient 12, and by following the path of the exhalation gases from the patient 12 to the ambient environment.

It is noted at the outset of the present description that certain components of the herein described ventilator system 10 are well known in the art. The function and structure of such known components is described in the ensuing specification only to the extent which is necessary to describe and explain the ventilator system 10, and its novel components and functions.

An air inlet filter 14 and an oxygen inlet filter 16 are shown schematically in the lower left corner of FIG. 1. The air filter 14 and the oxygen filter 16 receive a pressurized supply of air and oxygen, respectively. Air and oxygen which flow through the respective filters 14 and 16 enter, through check valves 18 and 20, into an air regulator 22 and an oxygen relay 24, respectively. The air and oxygen filters 14 and 16 prevent contamination of the ventilator system 10 by aerosols and particulates which may be present in the gases. The check valves 18 and 20 prevent cross-contamination of the air and oxygen sources.

Electric pressure switches 26 and 28 and pressure gauges 30 and 32 are interposed on the respective lines between the air filter 14 and air regulator 22, and the oxygen filter 16 and the oxygen relay 24. The pressure gauge 30 measures the actual pressure of air entering the air regulator 22, and pressure gauge 32 measures the actual pressure of oxygen which enters the oxygen relay 24. The pressure gauges 30 and 32 are preferably mounted on the exterior of the ventilator system 10, so that they can be readily observed by hospital personnel (not shown). Generally speaking, items shown outside of the broken line square box 33 on FIG. 1 are disposed on the exterior of the physical device which embodies the ventilator system 10.

Each of the pressure switches 26 and 28 provides an electric output signal schematically shown on FIG. 1 as 34 and 36, respectively, to the microcomputer controller 38 of the ventilator system 10, to indicate whether or not there is sufficient input pressure of the respective air and oxygen gas. More particularly, in the herein described preferred embodiment the pressure switches 26 and 28 are of the single pole, single throw type, and are preferably calibrated to close when the pressure falls below approximately $28 \pm 0.5$ pounds per square inch gauge (psig) pressure. When the switches 26 and 28 are open, (as they are during normal operation of the ventilator 10) they send the input signals 34 to 36 to the microcomputer controller 38. When either of the pressure switches is closed because of lack of sufficient pressure on the respective line, the switch sends a signal 34 or 36 directly to a cross-over solenoid valve 40.

The cross-over solenoid valve 40 is disposed between the lines leading from the check valves 18 and 20 to the air regulator 22 and oxygen relay 24, respectively. The cross-over solenoid 40 valve functions in the following manner: During normal operation of the ventilator system 10, the cross-over solenoid valve 40 is closed. When either the air or oxygen supply is interrupted, then the input 34 or 36 of the respective pressure switch 26 or 28 opens the cross-over solenoid valve 40. This permits air or oxygen, as applicable, to enter the air regulator 22, or oxygen relay 24, as applicable. As it will be readily understood from the ensuing description, the ventilator system 10 is able to function with an open cross-over solenoid valve 40 with either air or oxygen supply, although the oxygen concentration level in the respiratory gas delivered to the patient 12 may be compromised.

The above-mentioned filter, pressure switch, pressure gauge, regulator and solenoid valve components of the ventilator system 10 are substantially standard components of state-of-the-art ventilators, and require no detailed structural description. Preferably, the inlet filters 14 and 16 are capable of operating in the temperature range of −31 F. to +104 F., have a minimum of 98.5% retention of 0.4 micron sized (or larger) particles, or of 1 micron or larger droplets. The range of the pressure gauges 30 and 32 is preferably approximately 0 to 100 psig. The input pressure of the air and oxygen gases to the respective filters 14 and 16 is preferably in the 30 to 100 psig range, since at least 28±0.5 psig is required to keep the system 10 of the preferred embodiment operational.

The air regulator 22, also a substantially standard, state-of-the-art component of the system 10, is a precision instrument which is capable of outputting a substantially constant pressure of air in a wide flow range, preferably in the range of approximately 0 to 80 standard liters per minute (0 to 80 SLPM). In the herein described preferred embodiment, the air regulator 22 is calibrated and set to provide an output of air at 18.2±0.1 psig.

The oxygen relay 24, also a substantially standard, state-of-the-art component of the system 10, has similar output and pressure regulating characteristics to the air regulator 22. As is shown on the schematic view of FIG. 1, the oxygen relay 24 receives an input pilot pressure from the output of the air regulator 22 to slave the output pressure of the oxygen relay 24 to the air regulator 22. This is important, because in order to have accurate mixing or blending of the air and oxygen gases in the ventilator system 10, the pressures of the two gases must be substantially identical.

Following further the paths of the air and oxygen gases in the system 10, as schematically illustrated on FIG. 1, both gases enter a blender subsystem 44. For the purpose of distinct identification, the blender subsystem 44 is shown on FIG. 1 enclosed in a box 46 drawn with broken lines. The function of the blender subsystem 44 is to mix the air and oxygen gases in a ratio which is preselected by the microcomputer controller 38, in accordance with a "respiratory prescription" provided by a physician to suit the individual needs of the patient 12. Thus, the ratio of air and oxygen in the output of the blender subsystem 44 is a preselected control parameter of the ventilator system 10. This ratio is placed into the memory of the microcomputer controller 38 at a front or control panel (not shown) of the system 10.

The blender subsystem 44 incorporated in the ventilator system 10 of the present invention may be state-of-the-art. Preferably, however, the blender subsystem 44 incorporated in the present invention includes a single stage oxygen blending valve 48 which operates on the dual variable orifice principle, as is shown on the schematic view of FIG. 1. The pressure balanced air and oxygen lines are connected to separate ports 50 and 52, respectively, of the blending valve 48. A stainless steel ball 54 supported by a threaded shaft 56 and a spring loaded pin 57 diametrically opposite the shaft 56 moves back and forth between two seats 58 and 60, respectively, to simultaneously control the flow of the two gases. As the ball 54 is moved between the two seats 58 and 60 the flow area of one orifice is increased while that of the opposite one is reduced. Thus, the total effective flow area remains constant, regardless of the preselected setting of the blending ratio of the two gases.

The threaded shaft 56, and therefore the ball 54, are controlled through a flexible coupling 62 by the stepwise rotation of a stepper motor 64. The stepper motor 64 receives an input 66 from the microcomputer controller 38. This input 66 is responsive, in turn, to the output 68 of optical position sensors 70 which monitor the position of an optical disc 71 mounted to the shaft 56. The optical position sensors 70 are shown only schematically on FIG. 1.

Thus, the microcomputer controller 38 maintains the respiratory gas mixture exiting from the blending valve 48 at the preselected ratio of oxygen and air. As is known, this ratio may vary between approximately 21% $O_2$ (pure air) to approximately 100% $O_2$ (pure oxygen gas).

In the herein described preferred embodiment, the respiratory gas mixture enters into an accumulator 72 of approximately 3.6 liters volume, before it is released from the blender subsystem 44. The accumulator 72 enables the blender 44 to accomodate sudden demand surges for the respiratory gas.

Inasmuch as the present invention can be readily practiced with state-of-the-art blenders, further detailed description of the specific embodiment of the blender subsystem 44 is not deemed necessary here. Such a detailed description can be found in a co-pending application filed on the same date with the present application, assigned to the same assignee and titled Electronically Controlled Gas Blending System. The specification of this co-pending application is expressly incorporated herein by reference.

Referring still to the left side of FIG. 1, the conduit leading from the air regulator 22 to the pilot or control port of the oxygen relay 24 is shown to be tapped to lead air at the output pressure of the air regulator 22 (in the herein described preferred embodiment at 18.2±0.1 psig) to and through a drive valve 74. The output of the drive valve 74 is hereinafter referred to as system air, drive air, or system or drive pressure.

Another conduit, also tapped from the same source, leads air (at 18.2±0.1 psig) through a safety solenoid valve 76. The safety solenoid 76 receives its electric control signal 75 from the microcomputer controller 38. When the system 10 has an electric power failure, or the microcomputer controller 38 determines that the system is inoperative for other reasons, the control signal 75 closes the safety solenoid valve 76. Normally, the solenoid valve 76 is open and allows the pressurized air to pass through into the control or pilot pressure port 78 of the drive valve 74. Therefore, normally, the solenoid valve 76 allows pressurized air to flow through the drive valve 74. However, when the safety solenoid valve 76 is closed, the control port 78 of the drive valve 74 receives no pressure, and the drive valve 74 closes. Consequently, electric power failure, or any other inoperative state of the system 10 as determined by the microcomputer controller 38, results in loss of drive air or system pressure.

Similarly, if there is a "pressure failure" in the system, in the sense that the air regulator 22 fails to output pressurized gas, the drive valve 74 has no input and no output regardless of the functioning of the electrical portion of the system 10. As it is described further below, the drive air output of the drive valve 74 is used to drive the pilot pressure control valve of the present invention. Therefore, when there is no pressurized drive air, the artificial ventilation of the system 10 shuts down. In such a case, however, the patient 12 gains access, in a later described manner, to ambient air for spontaneous breathing.

More particularly, the blended respiratory gas is led to and through a flow shut-off valve 82. The control port 84 of the shut-off valve 82 receives the drive air at approximately 18 psig from the drive valve 74. If there is no pilot pressure for the control port 84, the shut-off valve 82 closes. Therefore, if the drive valve 74 has no pressure output, (there is no drive air) the respiratory gas cannot pass through the shut-off valve 82.

The respiratory gas passes from the shut-off valve 82 to a flow rate control subsystem 86 of the ventilator 10 of the present invention. The hereinafter described structure of the flow rate control subsystem 86 is novel.

The flow rate control subsystem 86 is enclosed on FIG. 1 in a box 87 drawn with broken lines. A portion of this subsystem is also shown on the cross-sectional view of FIG. 4. It includes a valve body 88 and a ball valve 90 which interfaces with a valve seat 92. Respiratory gas enters, at approximately 10 to 18 psig pressure, an inlet port 94 of the valve body 88 from the shut-off valve 82. The respiratory gas then passes through the valve formed by the ball 90 and the valve seat 92 and exits from the body 88 through the outlet port 96.

Figure 4:
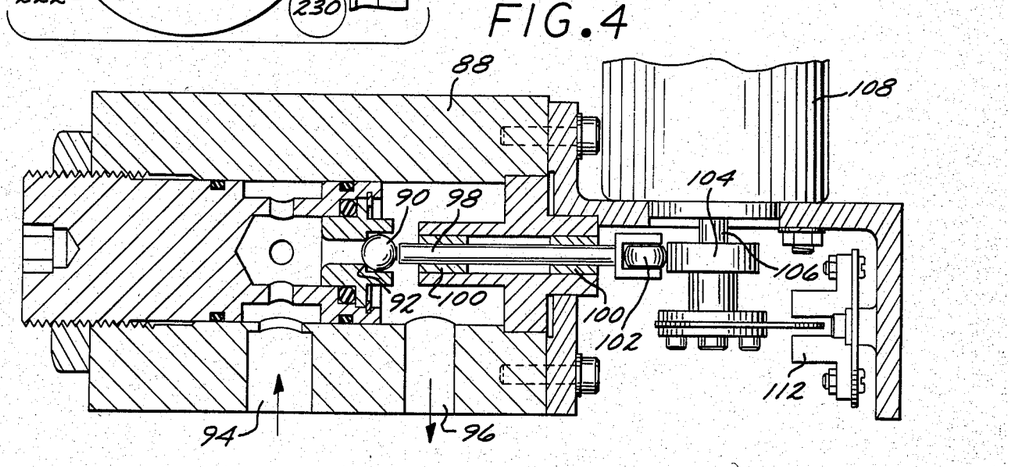
FIG. 4 is a cross-sectional view of the flow rate control subsystem of the present invention.

As is apparent from FIG. 4, the position of the ball valve 90 relative to the valve seat 92 is controlled by a rod 98 which is mounted in slider bearings 100. The rod 98 has a cam follower bearing 102 at its end remote from the ball 90. The cam follower bearing 102 interfaces with an asymmetrical cam 104 mounted to a shaft 106 of a second stepper motor 108. Because the gap between the ball 90 and the valve seat 92 is relatively small even in the fully open position of the valve, the pressure of the respiratory gas drops from approximately 10 to 18 psig to approximately 0 to 2 psig by passing through the valve body 88. Consequently, the pressure on the "high" pressure side of the body 88 presses the cam follower 102 against the asymmetrical cam 104, and no spring or like member is necessary to cause the cam follower 102 to accurately follow the cam 104.

The second stepper motor 108 is controlled by an electric input signal 110 of the microcomputer controller 38. In the herein described preferred embodiment, the stepper motor 108 has 189 steps of rotation which translate to 0.052 inch travel of the control rod 98. Thus, as it should already be apparent from the foregoing description, the stepper motor 108 controls the flow rate of respiratory gas through the valve body 88. The maximum open and fully closed positions of the valve in the body 88, which correspond to the 189 steps (less than one full rotation) of the stepper motor 108 are detected by optical sensors 112. The optical sensors 112 have light beams (not shown) which are interrupted only in the zero and full flow positions of the valve.

The structure and function of the optical sensors 112 incorporated in the flow control subsystem 86 are very similar to the optical sensors incorporated in the pilot pressure control valve of the ventilator 10 of the present invention. Further description of the optical sensors 112 is provided in this specification in connection with the pilot pressure control valve. It is sufficient to note for the purpose of describing the flow control subsystem 86 that an output 114 of the optical sensors 112 provides a reference point to the microcomputer controller 38 to establish and check the two respective extreme positions of the second stepper motor 108.

Referring now to the lower right side of the schematic view of FIG. 1, the respiratory gas is shown to flow from the outlet port 96 of the valve body 88 to a flow conditioner 116. The flow conditioner 116 is a state-of-the-art device which minimizes sonic noise and turbulence before the flow enters a flow transducer 118.

The flow transducer 118 is preferably of the type described in U.S. Pat. No. 3,680,375, the specification of which is incorporated herein by reference. The flow transducer 118 senses the instantaneous flow rate of the respiratory gas, and sends to the microcomputer controller 38 an electronic signal 120 indicative of the sensed flow rate.

The microcomputer controller 38 has stored in its memory, a predetermined flow rate-versus-time function. This function is used to provide a flow rate reference value when the ventilator is delivering a controlled breath, either at preselected time intervals, or in response to a proximal pressure drop indicative of a breathing attempt by the patient. when the ventilator is to deliver a "spontaneous" breath (one initiated and controlled by the patient), a flow rate algorithm stored in the microcomputer's memory provides a flow rate reference value which is a function of the patient's instantaneous demand, as measured by changes in the proximal pressure. In either case, the microcomputer controller 38 compares the signal 120 to a flow rate reference value which is required by the stored flow rate-versus-time function, or by the flow rate algorithm, and generates the control signal 110 which is responsive to the difference between the two values. The control signal 110 is sent to the second stepper motor 108 to control its position, and, if necessary, to adjust the flow rate to match the required value. The foregoing provides a substantially instantaneous servo control to assure precise adjustment of the flow rate.

Referring still to the right side of FIG. 1, a conduit is shown to lead from the output of the shut-off valve 82 to a purge/bleed valve 121, in parallel with the conduit leading to the flow control subsystem 86. The purge/bleed valve 121, thus receives respiratory gas at approximately 10 to 18 psig. The purge/bleed valve 121, which is of substantially standard, state-of-the-art construction, includes a throat 122, a diffuser 124, and two outlets, outlet 126 and orifice 128. In the herein described preferred embodiment the purge/bleed valve 121 is designed to permit an outflow of approximately 2 liters per minute (2 lpm) of respiratory gas through the outlet 126 to the ambient. This outflow occurs through an overboard exhaust outlet 130, which may simply be a tube (not shown specifically) discharging to the environment on the exterior of the ventilator device. The orifice 128 of the purge/bleed valve 121 provides, in the herein described preferred embodiment an average flow of approximately 0.13 lpm toward the patient 12.

In addition to the continuous flow of respiratory gas through the purge/bleed valve 121, there is a base line (bias) flow of approximately 5 lpm of the gas through the flow control subsystem 86. As will be readily understood from the ensuing description, the bias flow, when not inhaled by the patient 12, is allowed to escape to the environment during the exhalation cycle of the patient.

The continuous flow of respiratory gas through the purge/bleed valve 121 and the bias flow through the flow control subsystem 86 is desirable, because the blender subsystem 44 is unable to blend with sufficient accuracy when the flow is very small. Thus, the continuous flow permits the blender 44 to operate at sufficiently high flow rates to assure adequate blending accuracy.

The small (approximately 0.13 lpm or smaller) flow from the purge/bleed valve 121 toward the patient 12 keeps the proximal airway line 129 of the system 10 free of liquids and other material which may originate from the patient 12.

The respiratory gas is shown on FIG. 1 to enter from the flow transducer 118 into a safety valve subsystem 132. The safety valve 132 has a control or pilot pressure port 134 which receives drive air from the drive valve 74. When there is no input of pilot pressure to the pilot port 134, the safety valve 132 is open through a first outlet port 136 to the overboard exhaust outlet 130, that is to the ambient environment. However, when there is drive air or system pressure, the safety valve 132 is closed to the ambient and the respiratory gas flows through a second outlet port 138 of the safety valve 132 toward the patient 12. A one-way check valve 140 is disposed in the path of the respiratory gas in the safety valve 132 to prevent flow of gas in the opposite direction.

The respiratory gas flows from the safety valve subsystem 132 through an optional state-of-the-art bacterial filter 142 and a state-of-the-art humidifier 144.

A temperature sensor 146 is incorporated in the safety valve 132 in the path of the respiratory gas to provide an input signal 148 to the microcomputer controller 38. The temperature sensor 146 is important because the microcomputer controller 38 needs and uses its signal 148 to calculate the volume of gas delivered to the patient 12 under the medically accepted "body temperature, pressure, saturated" conditions.

A pressure transducer 150 is operatively connected to the safety valve 132 to continuously monitor the pressure therein, and to provide an input signal 152 indicative of the pressure to the microcomputer controller 38. The pressure which is present in the safety valve 132 is commonly termed "machine pressure". The machine pressure is an important parameter of the ventilation process in that it is normally only slightly higher than the proximal pressure of the patient 12. Therefore, the pressure transducer 150 functions as a back-up and check on the proximal pressure transducer which is described below.

The operation of the safety valve subsystem 132 should be readily apparent from the foregoing description, and inspection of the drawings. Thus, if there is no drive air, the safety valve 132 opens to provide a conduit through the first outlet port 136 to the ambient environment. Under these conditions the patient 12 is able to inhale ambient air through the safety valve 132. The one-way check valve 140, however prevents the patient 12 from exhaling through the safety valve 132. As it is described below, the patient 12 can always exhale through the exhalation valve of the ventilator 10 of the present invention, even in the event of electrical power or other system failure. The one-way check valve 140 also prevents water vapors from entering upstream into the system from a humidifier which is described below.

The respiratory gas flows from the humidifier 144 to a Y-tube 154 which is connected to inhalation tubes (not shown) of the patient 12, and to the exhalation valve. In the herein described preferred embodiment a bacterial filter 156 is interposed on the conduit between the purge/bleed valve 121 and the Y-tube 150.

The pressure which prevails in the Y-tube 154, or its vicinity, is commonly known in the art as "proximal pressure". As is readily understood by those skilled in the art, the proximal pressure is a very important parameter of the ventilator 10, and of the artificial ventilation process. The proximal pressure is continuously monitored, and it is displayed on a pressure gauge 158. The proximal pressure is also monitored by a pressure transducer 160 which provides to the microcomputer controller 38 an input signal 162 indicative of the proximal pressure.

Figure 2:
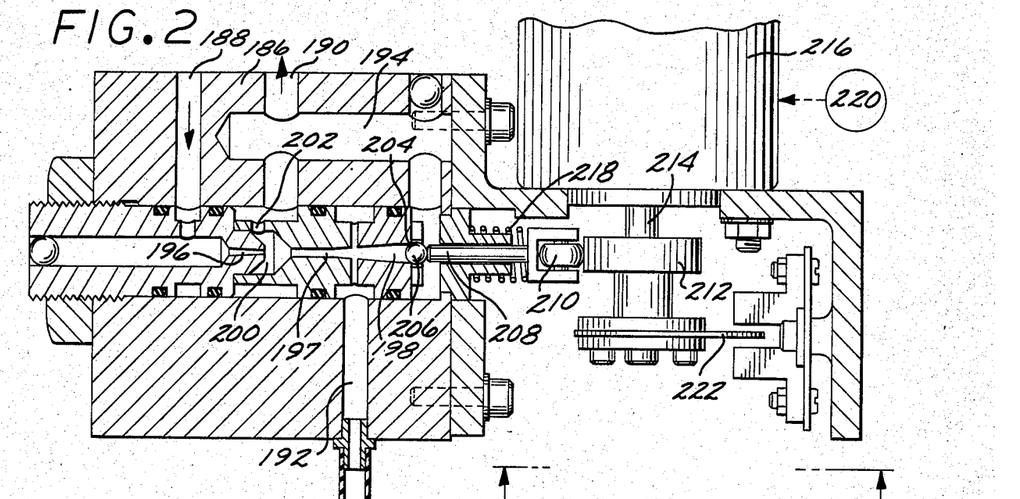
FIG. 2 is a schematic cross-sectional view of the pilot pressure control valve and exhalation valve of the preferred embodiment of the ventilator system of the present invention.

The exhalation valve 164 which is connected to the Y-tube 154 (patient circuit) with a conduit is shown in the upper right of FIG. 1 and, in more structural detail, in FIG. 2. The exhalation valve 164 may be constructed in accordance with the state of the art, as is shown on the drawing Figures. An exhalation valve which is particularly well adapted for use in the ventilator system 10 of the present invention, is described in detail in a co-pending application filed on the same date with the present application, assigned to the same assignee and titled Low-Noise Exhalation Valve For Medical Ventilator. The specification of this co-pending application is expressly incorporated herein by reference.

The exhalation valve 164 operates as a piloted relief valve. Thus, it has an inlet port 166, an outlet port 168 leading to a condensation trap 170, and a second outlet port 172 to a temperature controlled chamber 174. The exhaled gases, or gases otherwise vented from the patient circuit, escape from the temperature controlled chamber 174 to the ambient environment through an external flow transducer, schematically indicated on FIG. 1 as 176. The external flow transducer 176 provides to the microcomputer controller 38 an input signal 178 indicative of the flow rate of gases leaving the system 10. The temperature controlled chamber 174 is necessary, because, as is known in the art, the temperature of the flow transducer 176 must be elevated in order to prevent condensation.

A balloon valve, including a balloon 180 and a valve seat 182, is incorporated in the exhalation valve 164. The balloon 180 is controlled by a pilot pressure, which is the internal pressure in the balloon 180. When the pilot pressure exceeds the pressure in the exhalation valve 164, the balloon 180 inflates and seats against the valve seat 182 to block the flow of gas through the exhalation valve 164. If the valve 164 is of the type disclosed and claimed in the aforementioned co-pending application titled "Low-Noise Exhalation Valve For Medical Ventilator", then an aluminum or like metal plate 184 is molded integrally with the balloon 180 to seat against the valve seat 182 and to add rigidity and stability to the functioning of the valve.

The pilot pressure governing the balloon 180 controls the proximal pressure in the system in the sense that the proximal pressure cannot exceed the pilot pressure of the balloon 180. The structure of the pilot pressure control valve which controls the pilot pressure of the balloon 180 is a novel aspect of the present invention. Similarly, the manner in which the pilot pressure control valve interfaces and functions in the entire system 10 is considered novel.

Figure 3:
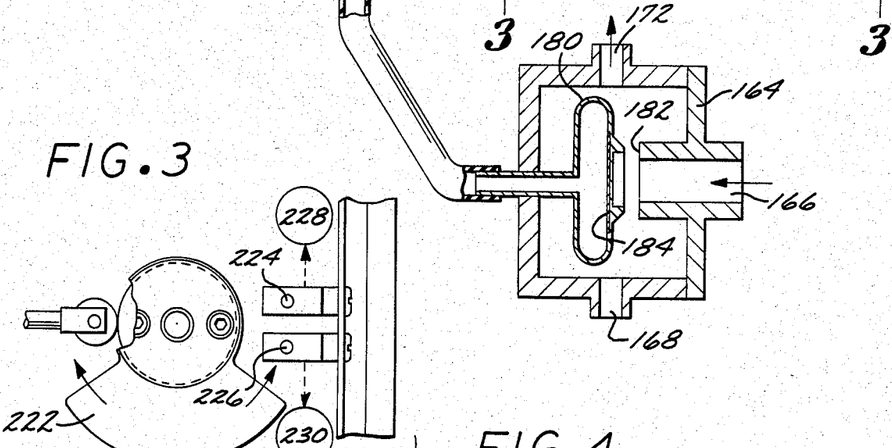
FIG. 3 is a plan view taken on lines 3,3 of FIG. 2.

Referring now principally to FIGS. 2 and 3, the pressure control subsystem 80 is shown to include a valve body 186, an inlet port 188, a first outlet port 190, a second outlet port 192 and an internal conduit or reservoir 194 for air. The inlet port 188 receives drive air or system air (at approximately 18 psig) from the drive valve 74.

The drive air flows from the inlet port 188 through a jet 196, a throat 197 and a diffuser duct 198. A chamber 200 surrounding the jet 196 is connected by another duct 202 to the internal conduit or reservoir 194. Depending on the flow rate of the gas, the gas around the jet periphery may be entrained with the jet flow causing a greater combined flow, or be flowing counter to the jet flow causing a lesser net flow. The air flow continues from the diffuser duct 198 through a valve, including a valve seat 204 and a ball 206, to the internal conduit 194. The first outlet port 190 leads from the internal conduit 194 to the ambient. The second outlet port 192 is disposed in the air flow between the jet 196 on the one hand, and the valve seat 204 and ball 206 on the other hand.

The position of the ball 206 relative to the valve seat 204 is regulated by a control rod 208 which is mounted in the valve body 186 for longitudinal motion relative to the ball 206 and the valve seat 204. The control rod 208 has a cam follower bearing 210 at its end which is remote from the ball 206. The cam follower 210 follows an asymmetrical cam 212 mounted to the rotatable shaft 214 of a third stepper motor 216. The cam follower 210 is urged against the cam 212 by a spring 218.

It should be apparent from the foregoing description and from an inspection of the relevant drawing Figures, that drive air flows from the inlet port 188 through the valve body 186 and the first outlet port 190 to the ambient. The flow rate of the air through the valve body 186 depends on the positioning of the ball 206 relative to the valve seat 204. The second outlet port 192, to which the balloon 180 of the exhalation valve 164 is connected, is merely a static port. There is a substantial pressure drop in the jet 196, so that the pressure in the static port 192 is significantly lower than the 18 psig incoming pressure of the drive air. Most importantly, from the standpoint of the present invention, the static pressure in the diffuser duct 198 and therefore in the second, static outlet port 192 depends on the flow rate, and therefore on the position of the ball 206 relative to the valve seat 204. The static pressure in the outlet port 192 is the pilot pressure for the balloon 180 of the exhalation valve 164.

In the herein described preferred embodiment, the jet orifice is 0.016 inch in diameter. The static port pressure-versus-ball position curve is not linear. In fact, it is possible for a negative (less than ambient) pressure to exist in the static port 192 when the valve is wide open (the ball 206 is far removed from the valve seat 204). An accurate pilot pressure-versus-ball position calibration curve is obtained within the practice of the present invention. This curve may be utilized in connection with the function of the microcomputer controller 38 which governs the pilot pressure control valve. In the operating range of the preferred embodiment, the pressure in the static port 192 varies between approximately zero to approximately 150 centimeters of water (cmH$_2$O).

Still further, in the preferred embodiment of the present invention, the asymmetrical cam 212 is constructed in such a manner that its configuration compensates for the non-linearity of the pilot (static port) pressure-versus-ball position relationship. In other words, the configuration of the cam 212 results in a substantially linear pilot pressure-versus-stepper motor step position relationship. Further adjustments to obtain a substantially linear and well defined pilot pressure-versus-stepper motor step position relationship can be made by moving (threading) the entire jet-throat assembly in or out until a desired zero point is achieved, and by adjusting the size of the orifice upstream of the jet 196.

The third stepper motor 216 is controlled by the output 220 of the microcomputer controller 38, to rotate the shaft 214, to linearly position the control rod 208 and the ball 206 into the position which provides the desired pressure in the static port 192. The output 220 of the microcomputer controller 38 is responsive to the input signal 162 received by the microcomputer controller 38 from the proximal pressure transducer 160.

The microcomputer controller 38 has stored in its memory, a predetermined pressure-versus-time function. This function is used to provide a pressure reference value when the ventilator is delivering a controlled breath, either at preselected time intervals, or in response to a proximal pressure drop indicative of a breathing attempt by the patient. When the ventilator is to deliver a "spontaneous" breath (one initiated and controlled by the patient), a pressure algorithm stored in the microcomputer's memory provides a pressure reference value which is a function of the patient's instantaneous demand, as measured by changes in the proximal pressure. The stored pressure function may be proximal pressure-versus-time function, or pilot pressure-versus-time function, or both. In this regard it is understood that proximal pressure may be below the pilot pressure. However, because of the particular nature of the exhalation valve 164, the proximal pressure cannot exceed the pilot pressure. Moreover, it should be understood that the pilot pressure-versus-time function may be relatively simple. For example, in machine controlled volume ventilation the pilot pressure may simply alternate, for predetermined periods of time, between zero and a constant pressure value. For machine controlled volume ventilation with positive end expiratory pressure (PEEP), the pilot pressure may alternate between a higher and lower pressure value, the lower one being the PEEP pressure value. Moreover, those skilled in the art will readily recognize that the preselected pilot pressure-versus-time function (as the flow rate-versus-time function) is fundamentally different for machine controlled breathing than it is for assisted or spontaneous breathing.

The microcomputer controller 38 compares the proximal pressure value derived from the input 162 of the pressure transducer 160 to the pilot pressure reference value required by the stored pressure-versus-time function, or by the pressure algorithm. The microcomputer controller 38 then generates an output signal 220 which is indicative of this difference, and which is used to control the third stepper motor 216.

As a refinement of the foregoing adjustment, the output signal 220 is used to adjust the stepper motor 216 only in the next cycle. This is desirable in order to avoid a situation where the flow control subsystem 86 and the pressure control subsystem 80 "fight" against one another. In other words, it is desirable to avoid a situation where the flow control subsystem 86 attempts to increase flow rate to raise the pressure in the system, and the pressure control subsystem 80 senses excess pressure and attempts to vent it by lowering the pilot pressure of the balloon 180. The stepper motor 216 used in the herein described preferred embodiment has 95 steps, corresponding to 0.026 inch of movement of the control rod 208.

As a further refinement of the pilot pressure control valve of the ventilator system 10 of the present invention, an optical disc 222 is mounted to the rotating shaft 214 of the third stepper motor 216. The optical disc 222 is actually a non-transparent or opaque element configured as a segment of a disc. Two optical sensors, schematically indicated on FIG. 3 as 224 and 226, are mounted adjacent to the shaft 214 in such a manner that the light beam (not shown) of one sensor is interrupted in each of the extreme positions of the shaft 214. Neither of the light beams is interrupted by the disc 222 when the shaft 214 is not in one of the two extreme positions.

The optical sensors 224 and 226 send to the microcomputer controller 38 a signal 228 or 230, respectively, to indicate that the shaft 214 has reached a respective extreme position. The signal 226 or 228 is then used by the microcomputer controller 38 to calculate the number of steps necessary to place the stepper motor 216 in the next desired position.

Referring now again principally to the exhalation valve 164, it is noted that in the total absence of pilot pressure, (such as in the case of a system malfunction) the balloon 180 functions as a one-way check valve. The balloon 180 does not permit the patient 12 to inhale through the exhalation valve 164. When the pilot pressure to the balloon 180 is zero because of system failure, the patient 12 inhales through the safety valve subsystem 132, and still exhales through the exhalation valve 164.

The microcomputer controller 38 of the ventilator system of the present invention need not be described here in detail. The hereinabove described functions of the microcomputer controller 38 may be accomplished, under the governance of appropriate software, by a general purpose computer or microprocessor and associated state-of-the-art electronics. The software can be generated by those skilled in the art on the basis of the above description of the functional aspects of the present invention.

Many modifications of the ventilator system 10 of the present invention may become apparent to those skilled in the art in light of the present disclosure. Therefore, the scope of the present invention should be interpreted solely from the following claims.

What is claimed is:

1. A ventilator system for providing artificial ventilation to a patient, comprising:
   means for providing a pressure regulated source of respiratory gas;
   flow control means for controlling the rate of flow of said respiratory gas in accordance with a predetermined flow rate-versus-time function, the flow control means receiving the gas from said source and being in fluid communication with the patient for transmitting the gas to the patient;
   exhalation valve means in fluid communication with the patient and with the flow control means for providing an outlet to the ambient for the proximal gases of the patient, said proximal gases including respiratory gas made available for breathing of the patient and gases exhaled by the patient, the exhalation valve means receiving an input pressure signal and being adapted for closing said outlet to the ambient when the input pressure signal exceeds the pressure of the proximal gases;
   pressure control means operatively connected with the exhalation valve means for providing said input pressure signal in accordance with a predetermined pressure-versus-time function, the pressure control means including venturi jet means receiving gas under substantially constant pressure, an outlet port for a stream of gas flowing in the venturi jet means to the ambient, a static port in fluid communication with said stream of gas to provide the input pressure signal, and means for regulating the flow rate of said stream of gas whereby the input pressure signal is regulated, the means for regulating including motor actuated means for interfering with the flow of the stream of gas in accordance with electric input signals received by the motor actuated means;
   pressure transducer means for sensing the instantaneous pressure of the proximal gases, and for generating electric signals indicative of said instantaneous pressure of the proximal gases, and
   computer means for receiving the electric signals from the pressure transducer means, for providing the predetermined pressure-versus-time function, for comparing the value required by said function to the instantaneous pressure of the proximal gases sensed by the pressure transducer means, and for generating and sending a corrective electric signal to the motor actuated means to regulate the flow of the stream of gas to adjust the input pressure signal to a value required by the predetermined pressure-versus-time function.

2. The ventilator system of claim 1 wherein the exhalation valve means include balloon valve means including a valve seat and a balloon which inflates and seats against the seat to close the outlet when the input pressure signal exceeds the pressure of the proximal gases.

3. The ventilator system of claim 1 wherein the motor-actuated means include a stepper motor having a shaft bearing an asymmetrical cam, a cam follower operatively connected to the cam to move linearly in accordance with the rotational position of the cam, and valve means connected to the cam follower for controlling the size of an opening in the venturi jet means whereby the pressure in the static port is regulated, the stepper motor receiving the corrective signals from the computer means and being controlled by said signals.

4. The ventilator system of claim 3 wherein the means for regulating include optical means for sensing the position of the cam of the stepper motor, and for providing an electric signal to the computer means indicative of said position.

5. The ventilator system of claim 4 wherein the cam of the stepper motor has two extreme positions and wherein the optical means are adapted for sensing said two extreme positions and for providing electric signals to the computer means indicative of the respective extreme positions of the cam.

6. The ventilator system of claim 5 wherein the computer means are adapted for sensing the unextended and fully extended positions of the cam follower from the signals sent by the optical means, and wherein the corrective signal to be sent to the stepper motor is generated relative to said extreme positions.

7. The ventilator system of claim 5 wherein the optical means include means for generating and detecting two light beams, and an optically opaque element mounted to the shaft of the stepper motor, one of the two light beams being interrupted by said optically opaque element in each respective extreme position of the cam.

8. The ventilator system of claim 1 wherein the flow control means include a chamber having an orifice wherethrough the respiratory gas flows, second valve means for adjustably restricting said orifice, and stepper motor means for operating the second valve means, and wherein the computer means are adapted for providing the predetermined flow rate-versus-time function and for sending a signal to the stepper motor means to operate the second valve means to provide an instantaneous flow rate corresponding to said flow rate-versus-time function.

9. The ventilator system of claim 8 wherein the flow control means include flow sensing means in serial fluid communication with the flow control means for sensing the flow rate of the respiratory gases downstream of the flow control means and for generating and sending an electric signal to the computer means indicative of the instantaneous flow rate of the respiratory gases.

10. The ventilator system of claim 9 wherein the computer means are adapted for generating and sending to the stepper motor means a second corrective electric signal responsive to the electric signal indicative of the instantaneous flow rate, said second corrective signal being proportional to the difference between the instantaneous flow rate and the flow rate required by the predetermined flow rate-versus-time function and causing the stepper motor to adjust said second valve means.

11. The ventilator system of claim 9 wherein the flow control means further include means for substantially eliminating sonic noise and turbulence in the flow of respiratory gases downstream of the second valve means and upstream of the flow sensing means.

12. The ventilator system of claim 8 wherein the stepper motor means include a stepper motor having a shaft bearing an asymmetrical cam, and a cam follower operatively connected to the cam to move longitudinally in accordance with the rotational position of the cam, the cam follower operating the second valve means.

13. The ventilator system of claim 12 further including optical means for sensing the position of the cam of the second stepper motor, and for providing an electric signal of the computer means indicative of said position.

14. The ventilator system of claim 13 wherein the cam of the second stepper motor has two extreme positions and wherein the optical means are adapted for sensing said two extreme positions and for providing electric signals to the computer means indicative of the respective extreme positions of the cam.

15. The ventilator system of claim 14 wherein the computer means are adapted for computing the unextended and fully extended positions of the cam follower from the signals sent by the optical means, and wherein the corrective signal to be sent to the second stepper motor is generated relative to said extreme positions.

16. The ventilator system of claim 15 wherein the optical means include means for generating and detecting two light beams, and an optically opaque element mounted to the shaft of the stepper motor, one of the two light beams being interrupted by said optically opaque element in each respective extreme position of the cam.

17. A ventilator system for providing artificial ventilation to a patient, comprising:
means for providing a pressure regulated source of respiratory gas;
flow control means for controlling the flow rate of the respiratory gas in accordance with a predetermined flow rate-versus-time function, the flow control means including adjustable valve means through which the respiratory gas flows to the patient and a stepper motor having a rotatable shaft, an asymmetrical cam mounted to the shaft, and a cam follower mounted for linear movement in relation to the valve means and operating the valve means to control the flow rate, the stepper motor being responsive to a first electric signal;
flow rate sensing and transducing means disposed downstream of the flow control means and in fluid communication therewith for sensing the flow rate of the respiratory gases and for generating a second electric signal indicative of the instantaneous flow rate of the respiratory gases;
exhalation valve means being in fluid communication with the patient and with the flow control means for providing an outlet to the ambient for the proximal gases of the patient, said proximal gases including respiratory gas made available for breathing of the patient and gases exhaled by the patient, the exhalation valve means receiving an input pressure signal and being adapted for closing said outlet to the ambient when the input pressure signal exceeds the pressure of the proximal gases;
pressure control means operatively connected with the exhalation valve for providing said input pressure signal in accordance with a predetermined pressure-versus-time function, and
computer means for receiving the second electric signal from the flow rate sensing and transducing means, for storing the predetermined flow rate-versus-time function, for comparing the value required by said function to the second electric signal generated by the flow rate sensing and transducing means, and for generating and sending the first electric signal, responsive to the second electric signal, to the stepper motor to regulate the valve means to adjust the flow rate to an instantaneous value required by the predetermined flow rate-versus-time function.

18. The ventilator system of claim 17 further comprising means disposed between the flow control means and the flow rate sensing and transducing means, for substantially eliminating sonic noise and turbulence in the flow of the respiratory gases.

19. The ventilator system of claim 17 further comprising pressure sensing and transducing means for sensing the instantaneous pressure of the proximal gases and for generating and sending to the computer means a third electric signal indicative of said instantaneous pressure.

20. The ventilator system of claim 17 wherein the flow control means include optical means for sensing the position of the cam of the stepper motor and for providing an electric signal to the computer means indicative of said position.

21. The ventilator system of claim 20 wherein the cam of the stepper motor has two extreme positions corresponding to the maximum and minimum flow rates of respiratory gases permitted by the adjustable valve means, and wherein the optical means are adapted for sensing said two extreme positions of the cam and for providing electric signals to the computer means indicative of the respective extreme positions of the cam.

22. The ventilator system of claim 21 wherein the computer means are adapted for computing the extreme positions of the adjustable valve means from the signals sent by the optical means, and wherein the first electric signal to be sent to the stepper motor is generated relative to said extreme positions.

23. The ventilator system of claim 22 wherein the optical means include means for generating and detecting two light beams, and an optically opaque element mounted to the shaft of the stepper motor, one of the two light beams being interrupted by said optically opaque element in each respective extreme position of the cam.

24. In a ventilator system for providing artificial ventilation to a patient including a pressure regulated source of respiratory gas; flow control means for controlling the flow of the respiratory gas in accordance with a predetermined flow rate-versus-time function; exhalation valve means in fluid communication with the flow of the respiratory gas and the patient for providing an outlet to the ambient for proximal gases of the patient, said proximal gases including the respiratory gas and the gases exhaled by the patient, and mixtures thereof, the exhalation valve means including means for receiving a pilot pressure and being adapted for closing the outlet to the ambient when the pilot pressure exceeds the instantaneous pressure of the proximal gases; pressure control means operatively connected with the exhalation valve means for providing the pilot pressure in accordance with a predetermined pressure-versus-time function; pressure transducer means for sensing the instantaneous pressure of the proximal gases and for generating a first electric signal indicative of said instantaneous pressure of the proximal gases, and computer means for receiving the first electric signal, for providing the predetermined pressure-versus-time function, for comparing the value required by the predetermined pressure-versus-time function to the instantaneous pressure of the proximal gases as indicated by the first electric signal, and for generating and sending a corrective second electric signal to the pressure control means to regulate the pilot pressure generated by the pressure control means, the improvement comprising:

means for providing a source of pressurized gas in addition to the respiratory gases provided for the patient;

venturi jet means included in the pressure control means for receiving the pressurized gas and having an outlet port to the ambient whereby a stream of gas flows through the venturi jet means, the venturi jet means further including a static pressure port wherefrom the pilot pressure for the exhalation valve means is tapped, and adjustable valve means included in the venturi jet means for regulating the stream of gas to the ambient whereby the pilot pressure is regulated, the adjustable valve means being controlled by the corrective electric signal generated by the computer means.

25. The improvement of claim 24 wherein the adjustable valve means include a stepper motor controlled by the corrective electric signal, the stepper motor having a rotatable shaft, an asymmetric cam mounted on the shaft, and a cam follower which operatively follows the cam to control the adjustable valve means.

26. The improvement of claim 24 further comprising optical sensing means for sensing the position of the shaft, for generating an electric signal indicative of the position of the shaft and for sending said signal to the computer means.

27. The improvement of claim 26 wherein the adjustable valve means have a first extreme position corresponding to maximum flow rate of the pressurized gas, and a second extreme position corresponding to a minimum flow rate of the pressurized gas, the rotatable shaft having two corresponding extreme positions, and wherein the optical sensing means are adapted for sensing the two extreme positions of the shaft.

28. The improvement of claim 27 wherein the shaft has an optically opaque element which rotates together with the shaft, and wherein the optical sensing means include means for generating and detecting two light beams, one of the two light beams being interrupted by said optically opaque element in each respective extreme position of the shaft.

29. The improvement of claim 27 wherein the computer means are adapted for sensing the first and second extreme positions of the valve means from the signals sent by the optical means, and wherein the corrective signal to be sent to the stepper motor is generated relative to the extreme positions of the shaft.

30. In a ventilator system for providing artificial ventilation to a patient including a pressure regulated source of respiratory gas; flow control means for controlling the flow of the respiratory gas to the patient in accordance with a predetermined flow rate-versus-time function; flow sensing and transducer means for measuring the flow rate of the respiratory gas downstream of the flow control means and for generating a first electric signal indicative of said flow rate; exhalation valve means in fluid communication with the flow of the respiratory gas and with the patient for providing an outlet to the ambient to proximal gases of the patient; pressure control means operatively connected with the exhalation valve means for controlling the exhalation valve means to maintain the proximal pressure in accordance with a predetermined pressure-versus-time function; and computer means for receiving the first electric signal, for providing the predetermined flow rate-versus-time function, for comparing the value required by the predetermined flow rate-versus-time function to the instantaneous flow rate as indicated by the first electric signal, and for generating and sending a corrective second electric signal to the flow control means to regulate the flow control means, the improvement comprising:

a stepper motor included in the flow control means and having a rotatable shaft, an asymmetric cam mounted to the rotatable shaft and a cam follower operatively mounted to follow the cam in a substantially linear motion, the stepper motor being controlled by the corrective second electric signal, and an adjustable flow control valve included in the flow control means and having an orifice interfacing with a valve body which is connected to the cam follower, whereby the stepper motor controls the flow rate.

31. The improvement of claim 30 further comprising optical means for sensing the position of the shaft of the stepper motor, for generating an electric signal corresponding to said position and for sending said electric signal to the computer means.

32. The improvement of claim 31 wherein the valve body has a first extreme position relative to the orifice corresponding to maximum flow rate of the respiratory gas, and a second extreme position corresponding to a minimum flow rate of the respiratory gas, the rotatable shaft having two corresponding extreme positions, and wherein the optical sensing means are adapted for sensing the two extreme positions of the shaft.

33. The improvement of claim 32 wherein the shaft has an optically opaque element which rotates together with the shaft, and wherein the optical sensing means include means for generating and detecting two light beams, one of the two light beams being interrupted by said optically opaque element in each respective extreme position of the shaft.

34. The improvement of claim 33 wherein the computer means are adapted for sensing the first and second extreme positions of the valve body from the signals sent by the optical means, and wherein the corrective signal to be sent to the stepper motor is generated relative to said extreme positions of the shaft.

* * * * *